(12) United States Patent
Allweier

(10) Patent No.: US 7,602,483 B2
(45) Date of Patent: Oct. 13, 2009

(54) DEVICE FOR DARK FIELD ILLUMINATION AND METHOD FOR OPTICALLY SCANNING OF OBJECT

(75) Inventor: Arnold Allweier, Allensbach (DE)

(73) Assignee: Chromasens GmbH, Constance (DE)

( * ) Notice: Subject to any disclaimer, the term of this patent is extended or adjusted under 35 U.S.C. 154(b) by 273 days.

(21) Appl. No.: 11/428,775

(22) Filed: Jul. 5, 2006

(65) Prior Publication Data

US 2007/0024846 A1 Feb. 1, 2007

(30) Foreign Application Priority Data

Jul. 6, 2005 (DE) ............... 10 2005 031 647

(51) Int. Cl.
*G01N 21/00* (2006.01)
(52) U.S. Cl. .................................... 356/237.4
(58) Field of Classification Search .... 356/237.1–237.6
See application file for complete search history.

(56) References Cited

U.S. PATENT DOCUMENTS

| 7,061,598 | B1 * | 6/2006 | Bevis et al. | 356/237.1 |
|---|---|---|---|---|
| 7,221,453 | B2 * | 5/2007 | Sharpe et al. | 356/338 |
| 2004/0075047 | A1 * | 4/2004 | Schnitzlein et al. | 250/234 |
| 2005/0001900 | A1 | 1/2005 | Kreh et al. | |
| 2005/0002023 | A1 | 1/2005 | Kreh et al. | |
| 2005/0259245 | A1 * | 11/2005 | Cemic et al. | 356/237.2 |

FOREIGN PATENT DOCUMENTS

| DE | 690 28 274 T2 | 4/1997 |
|---|---|---|
| EP | 0 426 166 B1 | 5/1991 |
| EP | 0 624 787 B1 | 11/1994 |
| EP | 1 150 154 B1 | 10/2001 |
| WO | 01/23869 A1 | 4/2001 |

OTHER PUBLICATIONS

Search Report from priority application No. DE 10 2005 031 647.6, filed Jul. 6, 2005.

* cited by examiner

*Primary Examiner*—Michael A Lyons
*Assistant Examiner*—Tri T Ton
(74) *Attorney, Agent, or Firm*—Houston Eliseeva LLP

(57) ABSTRACT

The invention relates to a device for dark-field illumination for an optical testing device for scanning a plane surface of an object together with a method for optical scanning of a plane surface of an object in which the device according to the invention is used. The illumination device according to the invention has a reflector which has in cross-section the form of a segment of an ellipse, while the illumination device may be arranged with a first focal point of the ellipse on the surface of the object, and the light source located at a point which results from reflection of the second focal point of the ellipse on the surface of the object. By this means, dark-field illumination with a high level of illumination at the first focal point is obtained, even when the light source is located a good distance away from the object.

16 Claims, 1 Drawing Sheet

DEVICE FOR DARK FIELD ILLUMINATION AND METHOD FOR OPTICALLY SCANNING OF OBJECT

RELATED APPLICATIONS

This application claims priority to Germany Application No. DE 10 2005 031 647.6, filed on Jul. 6, 2005, which is incorporated herein by reference in its entirety.

The present invention relates to a device for dark-field illumination for an optical testing device for scanning an object and a method for optical scanning of an object using such a device.

TECHNICAL BACKGROUND

It is known that wafers, mirrors, glass surfaces and printed circuit boards may be scanned optically by various methods. In these methods the object to be scanned, the wafer, mirror or the glass surface, is scanned by an optical line sensor, involving movement of the line sensor relative to the object, which generates a two-dimensional image. The line sensor is a colour sensor. The line on the surface of the object observed by the line sensor should be illuminated from different angles by light-emitting diodes, similarly arranged in lines, in the basic colours of the sensor, namely red, blue and green. Here at least one colour is used as bright-field illumination and another colour as dark-field illumination.

Bright-field illumination means that the light source on the surface of the object is reflected in the sensor. With dark-field illumination, there is no reflection of the light source relative to the sensor.

In the illumination of objects with reflecting surfaces, on the one hand the light source should lie as far as possible outside the sharp-focus range or focal plane of the sensor, i.e. the greatest possible distance should be maintained between the light source and the surface of the object. On the other hand, though, there should be a high level of light intensity on the surface of the object, for which reason it would be expedient to keep the distance between the light source and the surface of the object as low as possible. Moreover the object should be illuminated from different angles, so that any defect found is shown as clearly as possible. This is very difficult with the conventional light sources for illuminating a line, which generally consist of a light-emitting diode mounted along a line. These conflicting requirements, whereby the distance between the light source and the surface of the object should be on the one hand great and on the other hand small, are especially marked in the case of dark-field illumination of reflecting surfaces, where only a small fraction of the light-beam bundle directed on to the line to be scanned on the surface of the object is captured by the sensor.

In order to meet the requirements described above, an arrangement (FIG. 2) has been used to date in which, to illuminate a plane-surface object 1, one or more linear light sources 2 for dark-field illumination and a linear light source 3 for bright-field illumination are used. The light-beam bundle of the light source 3 for bright-field illumination is directed on to the line to be scanned on the surface of the object, from where it is reflected on to a mirror 4, from which the light-beam bundle is deflected to a line sensor 5. Typically used as line sensor is a one-dimensional colour CCD element with optics mounted in front. It is however also possible to use a camera which generates a two-dimensional image, of which only a single line is analysed. The light sources 2 for dark-field illumination are arranged very close to the surface of the object, so that a sufficiently high level of illumination is obtained.

However this has the consequence that the individual light-emitting diodes from which these linear light sources are formed are perceived by the camera as individual spots of light, since these light sources are located in the sharp-focus range of the sensor. Uniform and homogeneous illumination of the line to be scanned would be desirable, but is not possible with this arrangement of the dark-field illumination.

A further disadvantage lies in the fact that the dark-field illumination provides light only from the direction of the light sources. If the line to be scanned needs to be illuminated from a wider angular range, then either the luminous surface of the light source must be enlarged considerably, or else more light sources must be used.

Patent application US 2005/0001900 A1 discloses a device for the inspection of a wafer, comprising at least two incident illumination devices which emit an illuminating light beam which falls at an angle on the surface of a wafer to be inspected, determining in each case an illumination axis. An image recording device to record an image of the surface is provided in a dark-field array. Also provided is a wafer holding fixture to hold a wafer in a preset alignment. Formed on the surface of the wafer are linear structures. The device is characterised by the fact that the illumination axes are aligned at right-angles to one another and the device is so designed that a projection of the respective illumination axis is directed on to the surface of the wafer, substantially at right-angles to the respective linear structures on the surface of the wafer. The device may be used to detect macro-defects and to evaluate the quality of the edge profile of structures formed on the surface of the wafer.

Patent application US 2005/0002023 A1 discloses a device for the inspection of a wafer, comprising at least one incident illumination device which emits an illuminating light beam which falls at an angle on the surface of a wafer to be inspected, and an image recording device to record an image of the surface in a dark-field array. The wafer inspection device is distinguished by the fact that at least one deflecting device is provided to deflect an assigned illumination light beam on to the surface of the wafer.

Patent application US 2005/0259245 A1 discloses a device and a method for the inspection of an object, with a bright-field illumination beam path of a bright-field light source formed with reference to imaging optics, with a dark-field illumination beam path of a dark-field light source formed with reference to imaging optics, wherein the object with the imaging optics may be imaged on one or more detectors and wherein the object is illuminated simultaneously by both light sources. The device is suitable for simultaneous detection of bright-field and dark-field images.

Patent application WO 2001/023869 A1 discloses a device and a method for the finding and categorisation of surface defects of a moving belt material with an illumination device for generating an illumination surface (inspection surface). A camera set-up for recording an image of an inspection surface is provided, and the camera set-up is linked to a computing and control unit. At least one matrix camera is provided, for dividing the inspection surface image into at least two image sections for separate evaluation.

European patent EP 1 150 154 B1 relates to an arrangement and a method for illumination. Intended here in particular is incident illumination for microscopes, comprising a ring support—oriented around the optical axis—for holding means of illumination. According to the invention the illumination means are light-emitting semiconductor diodes (LEDs)

mounted in the ring support, wherein the main direction of radiation of the semiconductor diodes, which have a relatively small angle of departure, is directed or inclined towards the optical axis of the system. The diodes used are white-light diodes, preferably fixed in at least two concentric rows of rings within the ring support. Adjacent LEDs are connected into groups and are operated through a controllable constant current source.

Known from European patent EP 0 426 166 B1 is an illumination system in which three tungsten-halogen filament lamps are used to illuminate a linear section of an object. Two lamps are located close to the surface of the object, and are arranged parallel to the surface. Each of these two lamps is assigned a channel-shaped reflector with elliptical cross-section, by which the linear lamps are focussed on the linear area to be illuminated. The third lamp is arranged at a greater distance from the object. It is focussed on to the linear area to be illuminated by means of two reflectors. Here too, one of the two reflectors has an elliptical cross-section.

European patent EP 0 624 787 B1 shows a device for the surface inspection of silicon wafers. Here the wafer is illuminated at specific points. The light reflected from the wafer is deflected on to a photo-detector by means of an elliptical mirror, rotation-symmetric around an optical axis.

SUMMARY OF THE INVENTION

The invention is based on the problem of creating a device for dark-field illumination for an optical testing device for scanning an object and a method for optical scanning of an object using this illumination device. Also, by this means, a linear light source comprised of several light-emitting diodes is used to obtain homogeneous illumination of a line to be scanned on an object, with a high level of illumination.

The problem is solved by providing a device for dark-field illumination for an optical testing device for scanning an object, such as e.g. a wafer, a mirror or a glass plate, with a light source for dark-field illumination and a reflector, wherein the reflector has in cross-section the form of a segment of an ellipse, and the illumination device may be arranged with a first focal point of the ellipse on the surface of the object, and the light source is located at a point which results from reflection of the second focal point of the ellipse on the surface of the object.

The problem is also solved by a method in which the surface of an object to be scanned is scanned by a device for dark-field illumination, with a light source for dark-field illumination and a reflector, wherein the reflector has in cross-section the form of a segment of an ellipse, and the illumination device may be arranged with a first focal point (F1) of the ellipse on the surface of the object, and the light source is located at a point which results from reflection of the second focal point (F2) of the ellipse on the surface of the object.

Advantageous developments of the invention are set out in the dependent claims.

The device according to the invention for dark-field illumination for an optical testing device for scanning an object, such as e.g. a wafer or a printed circuit board, has a light source for dark-field illumination and a reflector.

According to the invention, the reflector has in cross-section the shape of a segment of an ellipse, which may be arranged with a first focal point of the ellipse on the surface of the object, and the light source is located at a point which results from reflection of the second focal point of the ellipse on the surface of the object.

If this illumination device is arranged with the first focal point on the point to be scanned on the surface of the object, then the light beams emitted by the light source for the dark-field illumination will be deflected on to the point on the object which is to be scanned, after a first reflection on the plane surface of the object and a second reflection at the reflector. By this means, virtually the whole of the amount of light radiated from the light source is directed on to the point or line to be scanned on the object. Moreover, the distance between the light source and the surface of the object need not be kept small, so that even when using a linear light source made up from several light-emitting diodes, a homogeneous light distribution is obtained.

For scanning an individual point on the surface of the object, the reflector is in the form of a segment of an ellipsoid, whereas the reflector for scanning a line is in the form of an elongated channel with the cross-sectional form of an ellipse segment.

Preferably the illumination device according to the invention also has a light source for bright-field illumination, with the light sources for dark-field illumination and bright-field illumination being located at similar distances from the point or line to be scanned.

According to the method according to the invention, the illumination device according to the invention is moved relative to the object to be scanned, with the first focal point being held on the surface to be scanned.

BRIEF DESCRIPTION OF THE DRAWINGS

The invention is explained below by way of example with the aid of the drawings, which show in.

PRECISE DESCRIPTION OF THE INVENTION

Figure 1:
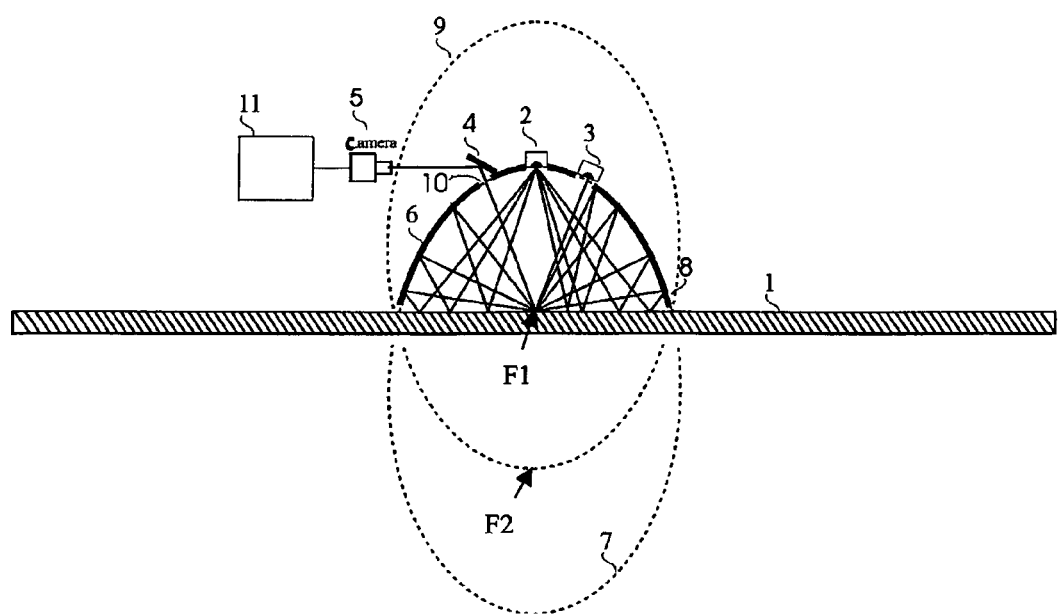
FIG. 1 the illumination device according to the invention in a sectional view together with an object to be scanned, and FIG. 2 a known arrangement for the illumination of an object to be scanned.
Figure 2:
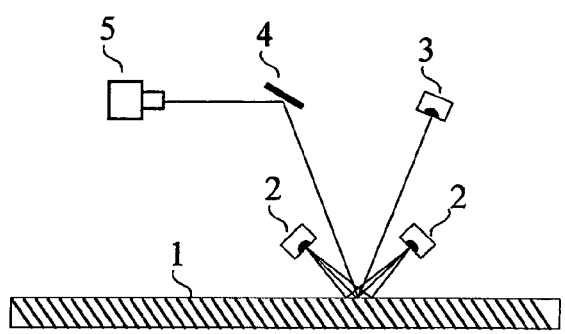

FIG. 1 shows an embodiment of an illumination device for the scanning of an object. This illumination device has a linear light source 2 for dark-field illumination, a linear light source 3 for bright-field illumination, and a mirror 4 to deflect light on to a line sensor 5.

According to the invention the illumination device is provided with a reflector 6 which has in cross-section the form of a segment of an ellipse 7. In this embodiment, the reflector 6 is elongated and channel-shaped.

The ellipse 7 has two focal points F1 and F2. The segment of the reflector 6 is so designed that it does not extend below the level of the upper focal point F1, i.e. the reflector has a lower boundary edge 8 at the level of the upper focal point F1 or somewhat above it. This makes it possible to arrange the illumination device on the object so that the focal point F1 is on the object surface to be scanned. The second focal point F2 of the ellipse 7 is located on the side of the surface to be scanned which faces away from the reflector. If this focal point F2 is reflected on to the object to be scanned, this gives the point at which the light source 2 for dark-field illumination is located. In the present embodiment, the light source 2 is located in the apex of the reflector 6. This arrangement also applies when the ellipse 7 is reflected at the surface to be scanned, which gives the reflected ellipse 9, while the light source 2 for dark-field illumination and the point or line to be scanned on the surface of the object 1 are each located at one of the two focal points of the reflected ellipse 9.

The light beams emitted by the light source 2 for dark-field illumination are reflected at the surface of the object 1 to be scanned to the reflector 6, and from the reflector 6 these light beams are reflected on to the line to be scanned in focal point F1.

Consequently almost all the light emitted by the light source 2 for dark-field illumination is directed on to the line to be scanned in focal point F1. Only minimal reflection losses reduce the amount of light arriving at focal point F1, compared with the amount of light emitted by light source 2.

Formed in the reflector 6 is an aperture 10, out of which the light reflected from the line to be scanned issues from the reflector 6. Located adjacent to this aperture is the mirror 4, which deflects the light on to the line sensor 5. Alternatively it is also possible to locate the sensor immediately adjacent to or in the area of the aperture. It is also possible to provide no aperture at all, and to locate the sensor inside the reflector 6.

In the present embodiment, the linear light source 2 is designed to emit blue light from a series of suitable light-emitting diodes. The linear light source 3 for bright-field illumination is designed to emit red light from a series of suitable light-emitting diodes. Since the two light sources 2, 3 give out light of different colours, a spectral separation of the bright-field and dark-field illumination is obtained. By this means a single sensor may be used to evaluate the bright-field illumination and the dark-field illumination separately from one another with the aid of a singe evaluation unit 11, to which the sensor 5 is coupled. In order to achieve this it is also possible to interchange the colours of the two light sources 2, 3.

The light source 3 for bright-field illumination is provided with a lens which bundles the radiated light and focuses it on the first focal point F1 of the reflector. By this means the amount of light emitted by the light source 3 is concentrated on the line of the object which is to be scanned.

In a simplified embodiment it is also possible to dispense with the light source for bright-field illumination and to replace the light source for dark-field illumination by a white radiating light source. Colour filters are then arranged in the channel reflector so that light which is directed from the reflector 6 on to focal point F1 and is reflected by the object 1 to the sensor 5, i.e. light reflected for instance from the area in which—in the embodiment above—the light source 3 for bright-field illumination is located, has a different colour from the other light.

In another simplified embodiment, again the light source for bright-field illumination is omitted. As the light source for dark-field illumination, a light source radiating blue light is used. In the area in which, in the embodiment shown in FIG. 1, the light source 3 for bright-field illumination is located, the channel reflector is provided with a coating which converts the short-wave blue light into longer-wave e.g. red light. This longer-wave light forms the bright-field illumination, while the light not converted by the coating forms the dark-field illumination.

With the illumination device according to the invention, even with a low reflection factor of the surface of the object 1, e.g. 30% to 40%, a luminance is obtained at focal point F1 which is distinctly higher than that from direct illumination. It may therefore be expedient, in particular for surfaces with very good reflective properties, to limit the angular range of the dark-field illumination by introducing matt areas to the reflector surface. The limitation may also be effected by providing the reflecting inner surface of the reflector 6 with a relatively low reflection factor of e.g. 50 to 70%. With the illumination device according to the invention, any defect present at focal point F1 will be illuminated from a greater angular range than with conventional methods, thereby giving a much more plastic image. It is therefore also much easier to detect in the course of evaluation.

Typically, a one-dimensional colour CCD element with a lens fitted in front is used as line sensor 5. This line sensor 5 and the associated lens form a line camera.

In the embodiment described above, the reflector 6 is symmetrical to a straight line or surface standing perpendicular to the object 1. It is however also possible to provide the symmetrical line or symmetrical surface of the reflector 6 at an angle to the surface of the object 1. In this case, though, the position of the light source 2 for dark-field illumination is correspondingly changed, so that it in turn adopts the location of the reflected second focal point F2.

To scan the surface of the object 1, the illumination device according to the invention is moved along the surface. Provided for this purpose is a slide unit (not shown) which also detects the current relative position between the reflector 6 and the object 1 and passes this information to the evaluation unit 11. With the aid of the current relative position between the reflector 6 and the object 1, the evaluation unit 11 covers the surface of the object 1 line by line, combining the individual lines to form a two-dimensional image or else two two-dimensional images, one for the bright-field illumination and one for the dark-field illumination. Using these images it is possible to determine whether there are defects on the surface of the object 1. This method is especially suitable for the scanning of highly reflective surfaces of wafers, mirrors or glass plates. It may however also be used for the scanning of surface of other objects such as e.g. printed circuit boards.

The invention may be briefly summarised as follows:

The invention relates to a device for dark-field illumination for an optical testing device for scanning a plane surface of an object together with a method for optical scanning of a plane surface of an object in which the device according to the invention is used. The illumination device according to the invention has a reflector which has in cross-section the form of a segment of an ellipse, while the illumination device may be arranged with a first focal point of the ellipse on the surface of the object, and the light source located at a point which results from reflection of the second focal point of the ellipse on the surface of the object. By this means, dark-field illumination with a high level of illumination at the first focal point is obtained, even when the light source is located a good distance away from the object.

LIST OF REFERENCE NUMBERS

| | |
|---|---|
| 1 | object |
| 2 | linear light sources for dark-field illumination |
| 3 | linear light sources for bright-field illumination |
| 4 | mirror |
| 5 | line sensor |
| 6 | reflector |
| 7 | ellipse |
| 8 | boundary edge |
| 9 | reflected ellipse |
| 10 | aperture |
| 11 | evaluation unit |

The invention claimed is:

1. Illumination device for dark-field illumination for an optical testing device for scanning an object with a light source for dark-field illumination and a reflector, wherein the reflector has in cross-section the form of a segment of an ellipse, and the illumination device is arranged with a first focal point (F1) of the ellipse on the surface of the object, and the light source is located at a point which results from reflection of the second focal point (F2) of the ellipse on the surface of the object,
  wherein the reflector is in the form of an elongated channel for scanning a line on the object,
  wherein the light source for dark-field illumination is located at the apex of the reflector,
  the illumination device further comprising a light source for bright-field illumination which is offset relative to the light source for dark-field illumination.

2. Illumination device according to claim 1,
  wherein the reflector is in the form of a segment of an ellipsoid.

3. Illumination device according to claim 1,
  wherein the light source for dark-field illumination and the light source for bright-field illumination emit light of different colors.

4. Illumination device according to claim 1,
  wherein the light source for bright-field illumination produces a light beam bundle, directed on to the first focal point (F1).

5. Illumination device according to claim 4,
  wherein the light source for dark-field illumination and the light source for bright-field illumination emit light of different colors.

6. Illumination device according to claim 1, further comprising:
  a single light source which emits white light, and
  at least one color filter that is arranged so that light which is reflected from one area of the reflector serving for bright-field illumination has a different color from the rest of the light.

7. Illumination device according to claim 1, further comprising:
  a single light source which emits blue light, and
  a coating on the reflector in a predetermined area which converts the light into longer-wave light, wherein the predetermined area of the reflector is the area used for bright-field illumination.

8. Illumination device according to claim 1,
  wherein the light source has one or several light-emitting diodes.

9. Illumination device according to claim 5,
  wherein the light source has one or several light-emitting diodes.

10. Illumination device according to claim 1,
  wherein there is provided an optical sensor, preferably located in the light beam bundle of the light source for bright-field illumination reflected at the object.

11. Illumination device according to claim 9,
  wherein there is provided an optical sensor, preferably located in the light beam bundle of the light source for bright-field illumination reflected at the object.

12. Illumination device according to claim 10,
  wherein the reflector has an optical aperture for the exit of a light beam bundle, which is directed on to the optical sensor.

13. Illumination device according to claim 11,
  wherein the reflector has an optical aperture for the exit of a light beam bundle, which is directed on to the optical sensor.

14. Illumination device according to claim 1,
  wherein the reflector is provided with matt areas in order to limit the angular range of the dark-field illumination.

15. Testing device for scanning the surface of an object, comprising
  an illumination device according to claim 1, and
  a slide unit for moving the illumination device relative to the object, and
  an evaluation unit for producing an image of the surface of the object with the aid of the relative position between the reflector and the object and the respective image data detected by the sensor.

16. Illumination device according to claim 1, wherein the object is one of a wafer, mirror, glass plate, or printed circuit board.

* * * * *